(12) United States Patent
Candau et al.

(10) Patent No.: US 6,322,798 B1
(45) Date of Patent: Nov. 27, 2001

(54) COSMETIC AND/OR DERMATOLOGICAL COMPOSITION WITH A HYDROPHILIC CARRIER AND VITAMIN C WHICH CAN BE MIXED IMMEDIATELY BEFORE USE

(75) Inventors: Didier Candau, Bievres; Nathalie Collin, Sceaux; Eric Quemin, Villepinte, all of (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 08/417,135

(22) Filed: Apr. 4, 1995

(30) Foreign Application Priority Data

Apr. 5, 1994 (FR) .................................................. 94 03982

(51) Int. Cl.[7] .............................. A61K 6/00; A61K 7/00; A61K 31/34
(52) U.S. Cl. ............................................. 424/401; 514/474
(58) Field of Search ............................... 424/401; 514/474

(56) References Cited

U.S. PATENT DOCUMENTS

| | | | |
|---|---|---|---|
| 4,487,757 | * 12/1984 | Kiozpeoplou | 424/7.1 |
| 4,711,780 | 12/1987 | Fahim | 424/145 |
| 4,818,521 | * 4/1989 | Tamabuchi | 424/62 |
| 4,983,382 | * 1/1991 | Wilmott et al. | 424/62 |
| 5,140,043 | * 8/1992 | Darr et al. | 514/474 |
| 5,455,035 | * 10/1995 | Guerrero et al. | 424/401 |

FOREIGN PATENT DOCUMENTS

| | | |
|---|---|---|
| A-36 42 097 | 6/1988 | (DE) . |
| A-0 399 157 | 11/1990 | (EP) . |
| A-0 401 454 | 12/1990 | (EP) . |
| WO-A-90 12572 | 11/1990 | (WO) . |
| WO-A-93 11737 | 6/1993 | (WO) . |

* cited by examiner

Primary Examiner—Thurman K. Page
Assistant Examiner—Amy Pulliam
(74) Attorney, Agent, or Firm—Oblon, Spivak, McClelland, Maier & Neustadt, P.C.

(57) ABSTRACT

A topical composition separately containing a hydrophilic carrier and a solid which are intended to be mixed immediately before use, the solid being powdered ascorbic acid and the carrier containing an aqueous medium and at least one hydrophilic gelling agent, the carrier being capable of withstanding the introduction of an acidic compound. In a preferred embodiment, the carrier (L) is packaged in a container (1) closed with a cap (3,6) containing ascorbic acid (P), a perforable and/or detachable separator (5) being provided between the acid and the carrier.

19 Claims, 1 Drawing Sheet

COSMETIC AND/OR DERMATOLOGICAL COMPOSITION WITH A HYDROPHILIC CARRIER AND VITAMIN C WHICH CAN BE MIXED IMMEDIATELY BEFORE USE

The present invention relates to a composition containing solid, preferably powdered, ascorbic acid and a hydrophilic carrier, the ascorbic acid and carrier being packaged separately and being capable of being mixed together just before use. The mixture is also described. This composition can be used in the cosmetic and/or dermatological fields by topical application to the skin both of the body and of the face, including around the eyes, and to the scalp.

The invention also relates to the use of the above composition and mixture for the cosmetic treatment of skin or for the preparation of an ointment for the dermatological treatment of the skin and/or mucous membranes, as well as to a process for the cosmetic treatment of the skin.

BACKGROUND OF THE INVENTION

Efforts have been made for a long time to formulate ascorbic acid (vitamin C) in the cosmetic and dermatological fields, in various galenic forms, because of its numerous beneficial properties. In particular, ascorbic acid stimulates the synthesis of connective tissue, in particular of collagen, enhances the defenses of skin tissue against damage by environmental agents such as ultraviolet radiation and pollution, compensates for any vitamin E deficiency of the skin, depigments the skin and has an anti-free radical function. These last two properties make it an excellent candidate as a cosmetic or dermatological active agent for combating and/or preventing skin ageing.

Unfortunately, because of its chemical structure (alpha-ketolactone), ascorbic acid is very sensitive to certain environmental parameters such as light, oxygen, water (through its pH and through the presence of traces of metals). The rapid degradation of ascorbic acid formulations occurs in the presence of these conditions, which is counter to the desired results. In order to reduce and/or retard the degradation of ascorbic acid, several solutions have already been envisioned in the prior art.

One of such solutions consists in blocking the reactive site of ascorbic acid, namely the hydroxyl site, especially by esterification or etherification with phosphated, sulphated or alkylated compounds (see in U.S. Pat. No. 5,087,446, JP-A-69/115558 and JP-A-83/129892 all incorporated herein by reference). Although more stable than ascorbic acid, these ascorbic acid derivatives are unfortunately much less effective than ascorbic acid itself.

Another solution consists in formulating the ascorbic acid in an acidic gel having a pH of not more than 3.5 and containing a high quantity of glycol, as described in WO-A-90/12572 incorporated herein by reference. Because of the acidic pH used and the presence of a large quantity of glycol, that is to say of solvent, this gel is poorly tolerated by the skin, whose pH is about 5.5. A repeated application of this gel to the skin causes irritation.

Another solution consists in using ascorbic acid in powdered form and in dissolving it in water just before use. Because of the high acidity of the solution obtained, it is aggressive and risks causing substantial irritation of the skin.

Another solution uses the freeze-drying of an aqueous solution containing an ester of ascorbic acid and hyaluronic acid; the freeze-dried product obtained is dissolved in water just before use. This solution has the disadvantages of being complex and quite expensive as well as using an ascorbic acid derivative which is less effective than that of ascorbic acid itself. In addition, the solution obtained is difficult to apply to the skin; it runs down the face and/or the body and is difficult to handle.

FR-A-2,645,740, incorporated herein by reference, describes a composition containing an oily phase, an aqueous phase and a solid phase to be mixed immediately before use, the solid phase containing one or more active agents (especially vitamin A) and an emulsifier, and being placed in the cap of a bottle containing the two liquid phases. This packaging allows a long storage time of the composition before mixing the three phases by shaking. After mixing, however, the composition is stable for only a few hours. Furthermore, the mixture obtained is a coarse emulsion which is not homogeneous. This results in lower efficacy; indeed, the coarser the emulsion, the less satisfactory it is as a vehicle for an active agent. In addition, the solid dissolves poorly. This three-phase composition cannot be used for an active agent with an acidic functional group, the acidic active agent carrying the risk of breaking the emulsion, or even of preventing its formation.

Other methods of stabilizing ascorbic acid include its coating (see, e.g., the technique described in FR-A-1,600,826 incorporated herein by reference). This technique is, however, on the one hand expensive and can, on the other hand, impair the ascorbic acid, for example during heating.

A topical composition for the hair, containing a solid product comprising an acid and a carbonate or bicarbonate, which are capable of reacting together, and a fluid carrier, is known from EP-A-399,157 incorporated herein by reference. This document teaches the formation of foam and consequently the necessary presence of carbonate or bicarbonate intended to react with the acid and does not teach the use of the acid alone in order to avoid its decomposition by the fluid carrier. The problem is therefore different in this case as compared to the present invention, as is the solution proposed.

OBJECTS OF THE PRESENT INVENTION

The need therefore remains for a cosmetic and/or dermatological composition containing ascorbic acid, capable of being stored for several years before being used, having especially the advantages of being nonirritating and effective, while being capable of being manufactured in a simple and inexpensive manner, especially for the purpose of large-scale production and which is easy to use by the user. These and other objects will become apparent from the following detailed description when taken in view of the Figure.

DETAILED DESCRIPTION OF THE INVENTION

Figure 1:
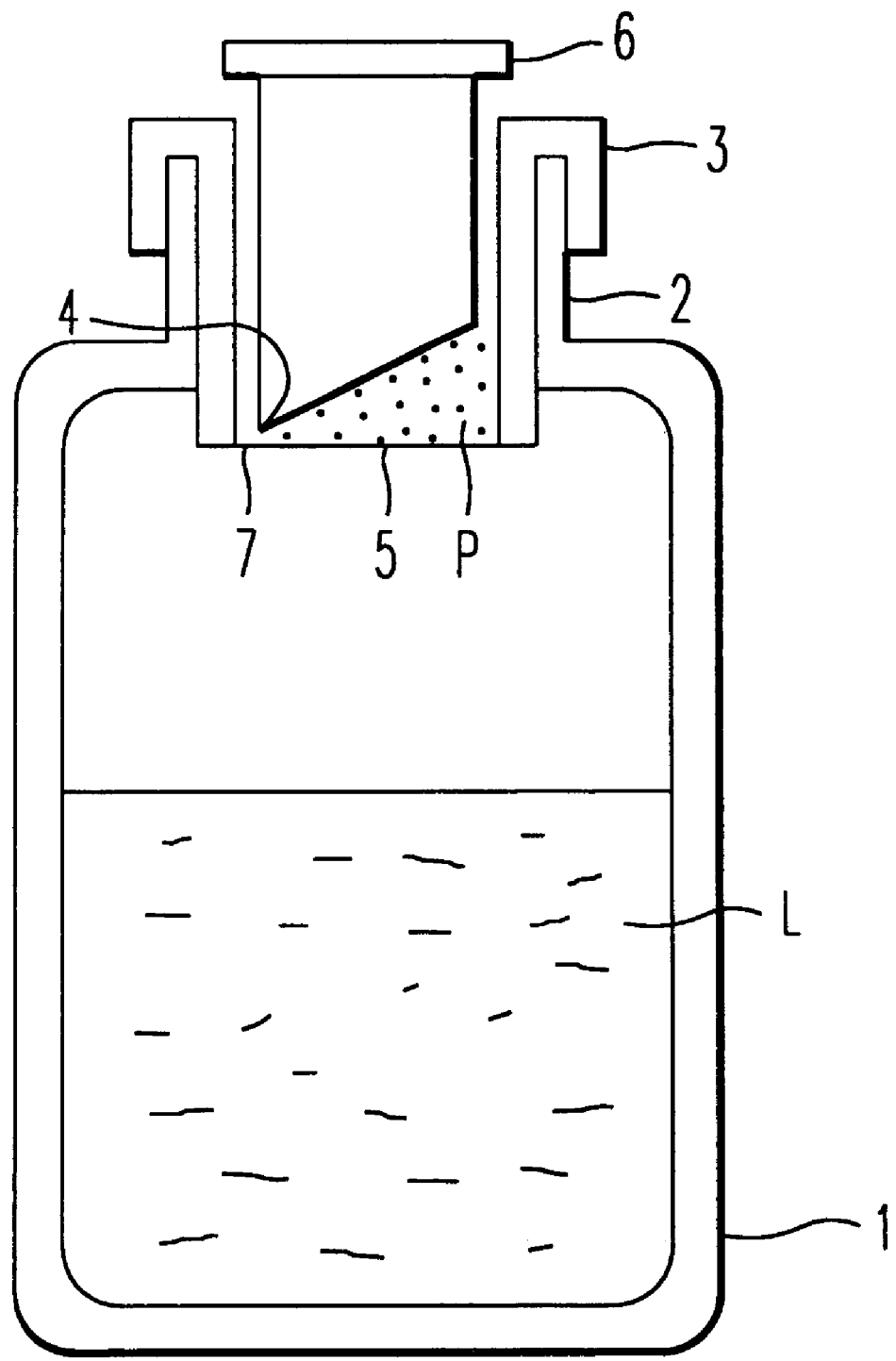
FIG. 1 shows a preferred embodiment of the present invention wherein carrier (L) is packaged in a container (1) closed with a cap (3,6) containing ascorbic acid (P), a perforable and/or detachable separator (5) being provided between the acid and the carrier.

The present invention provides a new cosmetic and/or dermatological topical composition containing a hydrophilic carrier and a solid. The two components are contained separately from one another but are intended to be mixed immediately before use. The solid comprises powdered ascorbic acid and the carrier comprises an aqueous medium and at least one hydrophilic gelling agent, the carrier being capable of withstanding the introduction of an acidic compound. In the present invention a carrier being capable of withstanding the introduction of an acidic compound is a carrier (e.g., a gel, an emulsion, etc.) which does not break and remains stable at room temperature for at least one week after the introduction of an acidic compound, such as after the introduction of from 0.001 to 0.1 grams of ascorbic acid per gram of carrier. The carrier of the invention is preferably one that loses, to degradation, etc., no more than 16%, preferably no more than 10%, of the initial amount of ascorbic acid present therein after eight days at room temperature. In contrast to the composition described in EP-A-399,157, the solid of the invention composition preferably contains only powdered ascorbic acid and/or is free of carbonate and bicarbonate.

The composition according to the invention is preferably to be mixed before use by simple manual shaking. The reconstituted product is stable, at room temperature, for at least one week, which is not the case for the mixture obtained according to FR-A-2,645,740. Moreover, the dissolution of ascorbic acid in the invention hydrophilic carrier occurs easily, without breaking the carrier. In addition, the carrier of the invention incorporates ascorbic acid in the protonated state, and thus the invention carrier offers more effective treatments than those of the prior art preparations containing ascorbic acid derivatives.

In order to facilitate the introduction of the ascorbic acid, the invention carrier should be relatively fluid. This fluidity makes it possible, in addition, to take up the carrier simply by passing the finger through it. In practice, the carrier has, before mixing, a viscosity in the range from 1 to 25 poises (0.1 Pa.s to 2.5 Pa.s) and preferably from 3 to 15 poises (0.3 Pa.s to 1.5 Pa.s).

Preferred hydrophilic carriers according to the invention include aqueous solutions of one or more hydrophilic gelling agents which can be used in the cosmetic and/or dermatological fields, of which at least one is capable of withstanding the introduction of an acidic compound. These gelling agents can be chosen from polysaccharides, synthetic polymers and celluloses, among others.

Examples of preferred gelling agents which can be used in the present invention include guar gums, xanthan gums, carrageenan, cellulose, hydroxyalkyl celluloses, sodium carboxycelluloses, SEPIGEL 305 (polyacrylamide/isoparaffin $C_{13}$–$C_{14}$/laureth-7) and others sold by the company Seppic, polyurethanes, E-8/94 from the company Hoechst (polyacrylamidomethylpropanesulphonic acid), gelatin, agar, starch, etc. The quantity of gelling agent is such that the carrier, before the introduction of the ascorbic acid, has the viscosity indicated above.

In order to avoid obtaining a carrier which is too acidic (i.e., a pH less than 3.5) after introducing the ascorbic acid, it is preferable to add to the carrier one or more pH-regulating agents. Examples of such agents include sodium citrate or sodium acetate buffer. The quantity of buffer is a function of the quantity of ascorbic acid used and the desired final pH; the latter is typically from 3.0 to 6, more preferably from 3.8 to 4.5 but including all values and all ranges therebetween.

The quantity of ascorbic acid present in the invention composition is preferably from 0.1% to 10% of the total weight of the composition, after mixing, preferably from 0.5% to 8%, more preferably from 2% to 6% but including all values and all ranges therebetween.

The invention hydrophilic carrier is preferably an aqueous gel optionally containing a dispersion of oil droplets, with or without emulsifier, this oil and emulsifier being selected such that the carrier is always compatible with the introduction of an acidic compound. A gelling emulsifier which can be used in the invention is SEPIGEL 305 and emulsified carriers according to the invention in which an acidic compound can be introduced include emulsions containing sugar derivatives, such as ARLATONE 2121 from ICI. These emulsions look like milk or a lotion. Oils which can be used in the invention include one or more of vegetable, synthetic, mineral, silicone and/or fluorinated oils.

Advantageously, and in order to avoid the presence in the aqueous phase of heavy metals which can catalyze the degradation of ascorbic acid after mixing the support and the solid, the hydrophilic carriers of the invention which comprise water are preferably formed from demineralized or deionized water. In order to further increase the stability of the ascorbic acid over time, the carrier of the invention may comprise, furthermore, a metal-sequestering agent such as a phosphonic acid derivative.

Phosphonic acid derivatives which can be used in the invention include ethylenediaminetetra (methylenephosphonic) acid, hexamethylenediaminetetra (methylenephosphonic) acid, diethylenetriaminepenta (methylenephosphonic) acid, and their salts, especially their sodium salt such as the pentasodium salt of ethylenediaminetetra- (methylenephosphonic) acid. For example, ethylenediaminetetra(methylenephosphonic) acid, sold by the Monsanto under the name DEQUEST 2041, may be used with advantage. The pentasodium salt, which is sold under the name Dequest 2046 by company Monsanto, can also be advantageously used. The quantity of sequestering agent is not limited but is in general at most equal to 0.5% of the total weight of the composition, and is preferably from 0.05% to 0.2% by weight.

The carrier of the invention may contain other additives apart from those mentioned above, which are generally used in the cosmetic and dermatological fields, such as antioxidants (such as pure ethoxyquin sold under the name of RALUQUIN by the Raschig), emollients, water-soluble active agents, preservatives (such as parabens and germal), perfumes, colorants (such as pigments and hydrophilic colorants) and fillers. The emollients are preferably polyols such as glycols (butylene glycol, isoprene glycol, propylene glycol and polyethylene glycols having 4 to 6 moles of ethyl oxide per unit) and glycerols. These emollients are advantageously present in an amount of 0% to 5% of the total weight of the composition.

The water-soluble active agents which can be used in the invention hydrophilic carrier are for example floral water, thermal water, plant extracts (aloes or hamamelis extracts which serve as anti-inflammatory agent and demulcent), D-panthenol (serving as anti-inflammatory agent), hydroxyproline (serving as repairing and cicatrizing active agent), urea and hyaluronic acid (serving as moisturizers). These active agents are in general used up to 1% of the total weight of the composition. However, the floral or thermal waters can replace all or part of the water of the aqueous medium used in the invention hydrophilic carrier.

In order to store the composition of the invention, before mixing the carrier and the solid, the carrier and ascorbic acid are kept separate from one another in two separate containers or, preferably one container. In using a single container the carrier may be packaged in the body of a container which is closed with a cap containing ascorbic acid, a perforable and/or detachable separator being provided between the acid and the carrier. These packagings include those described in FR-A-2,476,607, FR-A-2,453,793 or FR-A-2,645,740 all incorporated herein by reference. Given the sensitivity of the formulated vitamin C to light, it is preferable to use an opaque and/or amber-colored bottle, which does not allow damaging radiation to pass through.

The powdered ascorbic acid which may be used in the invention can be that which is sold by Hoffmann-LaRoche and is provided in the form of L-ascorbic acid with a purity of 99% to 100%. It is possible to use powdered D-ascorbic acid which is at least 99% pure, or a mixture of D- and L-forms of 99% or greater purity. Preferred particle diameters of the invention powdered ascorbic acid are ≦200 microns, preferably ≦150 microns.

The composition of the invention can be used as product for treating the skin and/or as dermatological product. In particular, the invention composition can be used for combating and/or preventing ageing, especially by reducing wrinkles, by attenuating or even eliminating spots which appear over time, by protecting the skin from UV radiation, by toning up the skin, by regenerating the skin tissues and by making the complexion brighter. The composition of the invention can also serve to cicatrize and/or asepticize sores. The invention composition defined above may be used for the cosmetic treatment of the skin and for toning it up, for regenerating it, for smoothing the wrinkles of the skin, for making the complexion lighter, for attenuating pigmented spots of the skin, and/or for combating the damage caused by UV radiation and/or for strengthening the skin tissues against damage by environmental agents.

The invention composition may also for the manufacture of an ointment intended for the dermatological treatment of the skin, such as cicatrization and asepticizing.

The present invention also includes a process of cosmetic treatment, comprising the step of applying to the skin, including around the eyes, the invention composition or ointment as described above.

Other characteristics and advantages of the invention will emerge more clearly from the description below, given as a guide and with no limitation being implied, with reference to the accompanying FIG. 1 which represents a longitudinal sectional view of a container (bottle) impervious to light, containing the composition of the invention, before mixing the carrier (a gel in this case) and the solid.

The gel and the solid which constitute the composition of the invention are packaged in a two-compartment container known in the art. The packaging shown in FIG. 1 is a simplified sectional view of a two-compartment bottle. It consists of a body (1) made from a material which serves as a shield against external light, and serving as a reservoir for fluid gel (L). In its upper part, the reservoir (1) is provided with a neck (2) into which is inserted a cup (3), closed at its lower part by a cover (5), in which cup the solid (P) is placed. The cover (5) can be molded into a single part with the cup (3) and preferably contains greatly weakened regions (7). It is also possible to heat seal an aluminum cover over the lower part of the cup.

Into the upper open part of cup (3) is tightly inserted a mixing device (6) provided at its lower part with a cutting region (4) capable of cutting an area of the cover (5) when the user pushes the mixing device (6) downwards. The downward movement of the mixing device (6) then causes tearing of the cover (5) and the solid (P) can flow into the fluid gel (L). Before use, the cup (3) provided with its mixing device (6) serves as cap for the container.

Before the application of the product, the user shakes the whole in order to dissolve the solid preferably consisting only of L-ascorbic acid which is at least 99% pure in the fluid gel and the mixing device (6) is then withdrawn from the cup (3) in order to free the distribution orifice. A soft plastic nipple, pierced at its end, can also be optionally added in order to facilitate the release of the product onto the skin.

Examples of compositions in accordance with the invention are given below. The quantities are given as percentage by weight of the total weight of the composition.

EXAMPLE 1

Buffered Gel with Vitamin C, pH=4

| Gel: | |
|---|---|
| Phase A | |
| Carrageenan | 1.5% |
| LUBRAJEL (glyceryl polynethacrylate) | 28.5% |
| Demineralized water | 69.8% |
| Sodium hydroxide | 0.5% |
| Phase B | |
| Demineralized water | 4.8% |
| Methylparaben (preservative) | 0.3% |
| DEQUEST 2046 | 0.1% |
| Aloe extract | 0.5% |
| Solid | |
| Ascorbic acid | 5% |

The gel is manufactured in a conventional manner by separately preparing phases A and B, respectively, at 70° C. and 40° C. by adding together the ingredients, then by adding phase B to phase A with shaking at 40° C. and by leaving the whole to cool, with gentle shaking, down to room temperature.

EXAMPLE 2

Buffered Gel with Vitamin C, pH=4

| Gel: | |
|---|---|
| Phase A | |
| Carrageenan | 1.3% |
| Guar | 0.5% |
| LUBRAJEL | 28.5% |
| Isoprene glycol | 4.8% |
| Demineralized water | 57.2% |
| Sodium hydroxide } | 0.8% |
| Citric acid } (pH regulator) | 1.2% |
| Phase B | |
| Demineralized water | 4.8% |
| Methylparaben | 0.3% |
| DEQUEST 2046 | 0.1% |
| Hamamelis extract in propylene glycol | 0.5% |
| Phase C | |
| Colorant | 0.04% |
| Phase D | |

-continued

| Gel: | |
|---|---|
| Perfume | 0.4% |
| Solid: | |
| Ascorbic acid | 5% |

Phases A, B, C and D are manufactured separately simply by mixing together the listed ingredients or providing the single ingredients at 70° C., 40° C., 40° C. (or 25° C.) and 40° C. (or 25° C.) respectively. Phase B is introduced into phase A at 40° C., then phases C and D are added, with stirring. The whole is allowed to return to room temperature, with slow stirring.

Sensory Analysis Test

The composition of Example 2 was tested on a panel of 31 judges for an entire day. The gel was judged to be fluid and jelly-like and was found to hold sufficiently upon taking up with the finger. Upon application, it is soft, not greasy and is light. It penetrates easily and does not lather at all. Moreover, the panel noted the good tensile and film-forming effect of the composition, and the general opinion was good.

Test of Use

A four week test using the invention composition as described in Example 2 was carried out on 14 women, 7 of which were aged from 30 to 49 years and 7 others were aged from 50 to 70 years. These women were experts in evaluating products for treating the face, half of whom had dry and very dry skin, the other half having greasy and combination skin.

On using the product over this time, these experts judged that the active ingredients therein would be well preserved and would remain active during the entire duration of use; the samples tested were intended for a treatment of one week. Moreover, they considered that the product, after mixing the solid and gelled phases, produced the following cosmetic properties:

toning, stimulation, regeneration, moisturizing of the skin;

firmness and fineness of the grain of the skin;

smoothness, softness and attenuation of wrinkles;

clarity and unification of the complexion, effect of looking well;

nutrition and comfort of dry skin;

fresh and light texture.

Test of Stability

The stability of the composition of Example 2 and that of a composition 3, identical to the composition of Example 2, with the exception of a pH of 3 and therefore a larger quantity of citric acid, were tested just after mixing the gel and the solid and 8 days later.

The results obtained are presented in the table below for 3 samples of each of these compositions.

| Comp-osition | Sample number | Theoretical level | CONTENT | |
|---|---|---|---|---|
| | | | T0 day (mean) | T8 days (mean) |
| No. 3 | a | 5% | 5.05 % Damaged bottle (4.81%) | Overdose due to non-impervious bottle (4.69%) |

-continued

| Comp-osition | Sample number | Theoretical level | CONTENT | |
|---|---|---|---|---|
| | | | T0 day (mean) | T8 days (mean) |
| | b | 5% | 4.98% | 4.83% |
| | c | 5% | 4.64% | 4.54% |
| No. 2 | d | 5% | 4.79% | 4.35% |
| | e | 5% | 4.72% (4.80%) | 4.60% (4.37%) |
| | f | 5% | 4.89% | 4.15% |

According to this table, it can be observed that ascorbic acid is slightly more stable in the most acidic composition. However, the loss of ascorbic acid in the composition of Example 2 is only 9% after 8 days.

This application is based on French Application 94-03982 filed Apr. 5, 1994, incorporated herein by reference.

What is claimed as new and desired to be secured by Letters Patent of the United States is:

1. A composition, comprising a container having two compartments:
   (a) a first compartment containing a liquid component comprising a hydrophilic carrier, the carrier comprising water and at least one hydrophilic gelling agent;
   (b) a second compartment consisting of solid powdered ascorbic acid; and
   wherein liquid component (a) and solid component (b) are separate from one another.

2. The composition according to claim 1, wherein the carrier is an aqueous gel.

3. The composition according to claim 1, wherein the carrier has a viscosity in the range of from 1 to 25 poises.

4. The composition according claim 1, wherein the ascorbic acid represents from 0.1% to 10% of the total weight of the composition.

5. The composition according to claim 1, wherein the ascorbic acid represents from 2% to 6% of the total weight of the composition.

6. The composition according to claim 1, wherein the gelling agent is selected from the group consisting of polysaccharides, synthetic polymers and celluloses.

7. The composition according to claim 1, wherein the carrier further comprises a pH-regulating agent.

8. The composition according to claim 1, wherein the carrier further comprises at least one additive selected from the group consisting of sequestrants, antioxidants, emollients, water-soluble active agents, preservatives, perfumes, colorants, fillers, oils and emulsifiers.

9. The composition according to claim 1, wherein the carrier is packaged in a container closed with a cap containing said ascorbic acid, a perforable and/or detachable separator being provided between the acid and the carrier.

10. An ointment intended for dermatological treatment of the skin comprising the composition of claim 1.

11. A method for cosmetic or dermatological treatment of skin comprising the steps of mixing the solid and carrier components of the composition of claim 1 together and applying the mixture to the skin.

12. The composition according to claim 1, wherein the solid component consists of powdered ascorbic acid.

13. The composition according to claim 1, wherein the carrier is a gel or emulsion which remains stable after the introduction of from 0.001 to 0.1 grams of ascorbic acid per gram of carrier for one week at room temperature.

14. The composition according to claim 7, wherein the pH-regulating agent is a buffer and the pH of the carrier is 3–6.

15. The composition according to claim 14, wherein the pH of the carrier is 3.8–4.5.

16. The composition according to claim 1, wherein the powdered ascorbic acid has a particle diameter ≦200 microns.

17. The composition according to claim 1, wherein the ascorbic acid is L-ascorbic acid.

18. The composition according to claim 8, wherein the additive is a metal-sequestrant.

19. The composition according to claim 18, wherein the metal-sequestrant is a phosphonic acid.

* * * * *

UNITED STATES PATENT AND TRADEMARK OFFICE
CERTIFICATE OF CORRECTION

PATENT NO.    : 6,322,798 B1
DATED         : November 27, 2001
INVENTOR(S)   : Candau et al.

It is certified that error appears in the above-identified patent and that said Letters Patent is hereby corrected as shown below:

<u>Column 8,</u>
Line 20, "comprising" should read -- comprised within --; and
Line 33, after "according" insert -- to --.

Signed and Sealed this

Eighteenth Day of June, 2002

*Attest:*

*Attesting Officer*

JAMES E. ROGAN
*Director of the United States Patent and Trademark Office*